(12) United States Patent
Linsacum et al.

(10) Patent No.: US 9,167,179 B2
(45) Date of Patent: Oct. 20, 2015

(54) ON-BOARD NON-UNIFORMITY CORRECTION CALIBRATION METHODS FOR MICROBOLOMETER FOCAL PLANE ARRAYS

(75) Inventors: Deron L. Linsacum, Corona, CA (US); Nils A. Lavik, Aliso Viejo, CA (US); Greg Kwan, Fountain Valley, CA (US)

(73) Assignee: Vectronix, Inc., Bedford, NH (US)

( * ) Notice: Subject to any disclaimer, the term of this patent is extended or adjusted under 35 U.S.C. 154(b) by 769 days.

(21) Appl. No.: 13/371,414

(22) Filed: Feb. 11, 2012

(65) Prior Publication Data

US 2012/0211648 A1 Aug. 23, 2012

Related U.S. Application Data

(60) Provisional application No. 61/444,970, filed on Feb. 21, 2011.

(51) Int. Cl.
| | |
|---|---|
| *G01D 18/00* | (2006.01) |
| *G12B 13/00* | (2006.01) |
| *H04N 5/33* | (2006.01) |
| *H04N 5/365* | (2011.01) |
| *G01J 5/52* | (2006.01) |
| *H04N 5/361* | (2011.01) |
| *G01J 5/00* | (2006.01) |

(Continued)

(52) U.S. Cl.
CPC . *H04N 5/33* (2013.01); *G01J 5/522* (2013.01); *H04N 5/361* (2013.01); *H04N 5/3651* (2013.01); *H04N 5/3655* (2013.01); *G01J 2005/0048* (2013.01); *G01J 2005/0077* (2013.01); *G01J 2005/106* (2013.01); *G01J 2005/202* (2013.01); *G01N 2201/1211* (2013.01); *G01N 2201/12707* (2013.01); *G01N 2201/12715* (2013.01); *G01N 2201/12746* (2013.01); *G01N 2201/12753* (2013.01)

(58) Field of Classification Search
CPC ....... G01J 5/00; G01J 2005/0048; G01J 5/20; G01J 2005/202; G01J 5/52; G01J 5/522; G01N 2201/12; G01N 2201/121; G01N 2201/1211; G01N 2201/127; G01N 2201/12707; G01N 2201/12715; G01N 2201/12746; G01N 2201/12753; G01D 18/00; G01D 18/008; G06F 11/00; G06F 11/002; G06F 13/00
USPC .............................................. 250/252.1, 232
See application file for complete search history.

(56) References Cited

U.S. PATENT DOCUMENTS

| | | |
|---|---|---|
| 5,021,663 A | 6/1991 | Hornbeck |
| 5,286,976 A | 2/1994 | Cole |
| 5,300,915 A | 4/1994 | Higashi et al. |

(Continued)

*Primary Examiner* — David Porta
*Assistant Examiner* — Carolyn Igyarto
(74) *Attorney, Agent, or Firm* — Downs Rachlin Martin PLLC

(57) ABSTRACT

On-board non-uniformity correction calibration methods for a microbolometer focal plane array in a thermal camera are disclosed. The methods include performing first calculations in the processor unit of the thermal camera to generate and apply a set of coarse correction bias voltages to the detector elements. The method also includes performing calculations in the external computer based on image data collected by the thermal camera with the coarse correction bias voltages applied to the detector elements to generate a set of fine correction bias voltages. The method also includes downloading the fine correction bias voltages to the thermal camera and applying the fine correction voltages to the detector elements to establish a fine calibration of the microbolometer focal plane array.

17 Claims, 6 Drawing Sheets

(51) Int. Cl.
  *G01J 5/20* (2006.01)
  *G01J 5/10* (2006.01)

(56) References Cited

U.S. PATENT DOCUMENTS

| | | |
|---|---|---|
| 5,420,419 A | 5/1995 | Wood |
| 5,756,999 A | 5/1998 | Parrish et al. |
| 5,811,808 A | 9/1998 | Cannata et al. |
| 6,023,061 A | 2/2000 | Bodkin |
| 6,028,039 A | 2/2000 | Cane et al. |
| 6,444,983 B1 | 9/2002 | McManus et al. |
| 6,690,013 B2 | 2/2004 | McManus |
| 6,875,979 B2 | 4/2005 | Cope |
| 7,030,378 B2 * | 4/2006 | Allen et al. ............ 250/332 |
| 2002/0125430 A1 * | 9/2002 | Wood ............ 250/338.1 |
| 2003/0160171 A1 | 8/2003 | Parrish et al. |
| 2004/0200961 A1 | 10/2004 | Parrish et al. |

* cited by examiner

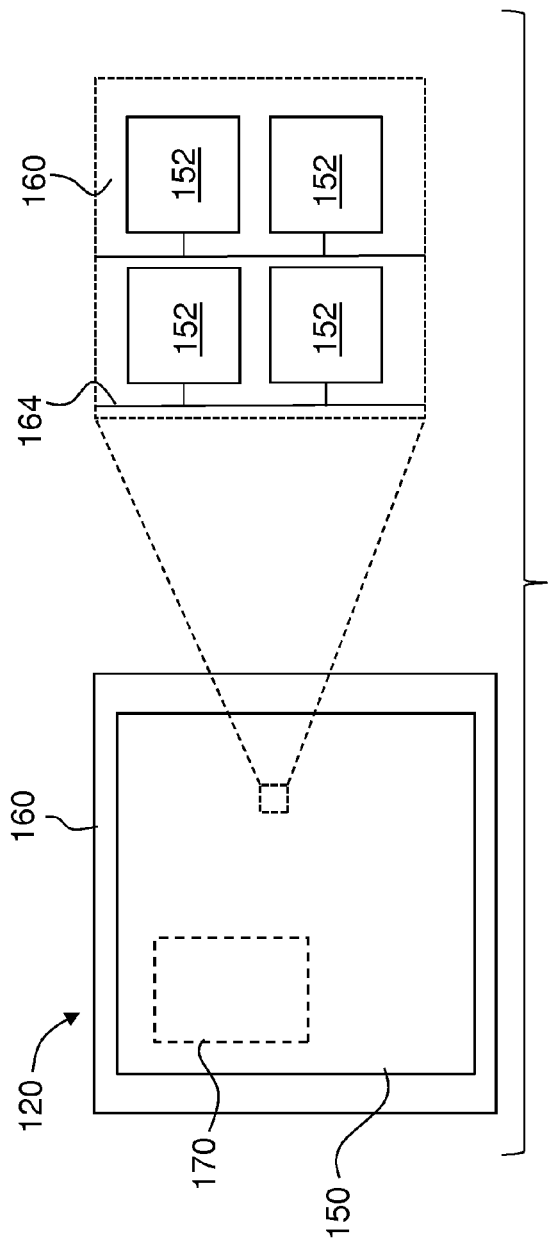
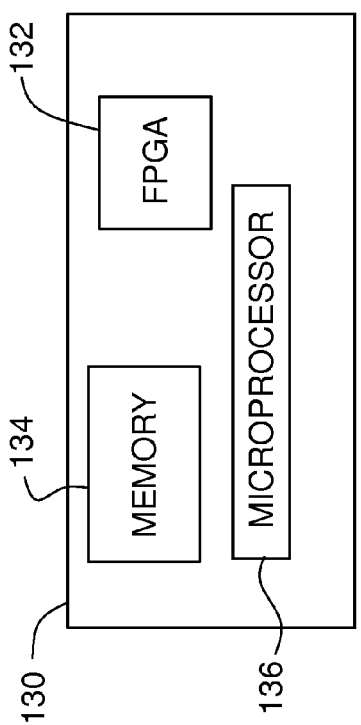
FIG. 3
FIG. 4

ON-BOARD NON-UNIFORMITY CORRECTION CALIBRATION METHODS FOR MICROBOLOMETER FOCAL PLANE ARRAYS

CROSS-REFERENCE TO RELATED APPLICATIONS

This application claims the benefit of priority under 35 U.S.C. §119(e) of U.S. Provisional Application Ser. No. 61/444,970, filed on Feb. 21, 2011, which is incorporated herein by reference.

FIELD

This disclosure relates generally to the field of calibration methods for focal plane arrays (FPAs), such as MFPAs, and in particular relates to methods for the calibration of multiple microbolometer detector devices using an on-board processor.

BACKGROUND ART

A microbolometer is an elemental infrared detector that utilizes a material whose electrical resistance changes as a function of temperature. This characteristic is used to measure amounts of infrared radiation incident on the microbolometer. When used as an infrared detector, a microbolometer is generally thermally isolated from its supporting substrate or surroundings to allow the absorbed incident infrared radiation to generate a temperature change in the bolometer material, and be less affected by substrate temperature. Example microbolometers are described in U.S. Pat. Nos. 5,021,663; 5,286,976; 5,300,915; 5,420,419; 5,756,999; 5,811,808; and 6,023,061, each of which is hereby incorporated by reference.

Microbolometer detector arrays are used to sense incident infrared radiation at a focal (or image) plane. Each microbolometer detector element in the array absorbs some of the infrared radiation resulting in a corresponding change in the pixel temperature, which results in a corresponding change in resistance. With each microbolometer detector element functioning as a pixel, a two-dimensional image or picture representation of the incident infrared radiation is generated by translating the changes in resistance of each microbolometer detector element into a time-multiplexed electrical signal that can be displayed on a monitor or stored in a computer.

The circuitry used to perform this translation can be called detector array interface circuitry (DAIC) and typically fabricated as an integrated circuit on a silicon substrate. The microbolometer can be fabricated on top of the DAIC. The combination of the DAIC and microbolometer array is commonly known as a microbolometer infrared Focal Plane Array (FPA), or simply MFPA for short. MFPAs can contain, for example, 640×480 microbolometer detector elements.

Certain types of thermal cameras employ MFPAs as the image sensor. However, the microbolometer detector elements of the MFPA will have non-uniform responses to uniform incident infrared radiation, even when the bolometers are manufactured as part of a MFPA. This is due to small variations in the detectors elements' electrical and thermal properties as a result of the manufacturing process. These non-uniformities in the microbolometer response characteristics must be corrected to produce an electrical signal with adequate signal-to-noise ratio for image processing and display as part of the thermal camera operation.

Methods for implementing a DAIC for microbolometer arrays have used an architecture wherein the resistance of each microbolometer is sensed by applying a uniform electric signal source (bias), e.g., voltage or current sources, and a resistive load to the microbolometer detector element. The current resulting from the applied voltage (bias) is integrated over time by an amplifier to produce an output voltage level proportional to the value of the integrated current. The output voltage is then multiplexed to the signal acquisition system.

Gain and offset corrections are applied to the output signal to correct for the non-uniformity. This process is commonly referred to as two-point correction. In this technique, two correction coefficients are applied to the sampled signal of each microbolometer detector element. The gain correction is implemented by multiplying the output voltage by a unique gain coefficient. Likewise, the offset correction is implemented by adding a unique offset coefficient to the output voltage.

Blind (reference) non-uniformity corrections (NUCs) are currently generated in an FPA calibration process by the following process: 1) start with default NUCs stored in the camera's memory, (e.g., flash memory); 2) iteratively capture an image; 3) upload the captured image to external computing resources, such as a personal computer for calculation; 4) generate a set of refined NUCs; 5) download the refined NUC data back into the thermal camera; and 6) write the corrections to flash memory in the thermal camera.

For a specific temperature point in the temperature range at which a MFPA is calibrated, the prior art method of capture/ upload/calculation/download/flash-write may be performed up to eighty times. This approach requires considerable time and related expense. Almost half of that calibration time is spent on pixel characteristic/response data collection and processing. The other half is spent on environmental temperature chamber settling time necessary for each new temperature set-point. The calibration processing system typically comprise a communication link between the thermal camera and an external calibration computer running a specialized software suite, such as a LabView® application. This MFPA calibration process is a relatively long and tedious task, with the various steps consuming up to ten hours for a single MFPA over at temperature range from −20° C. to 52° C. in 4° C. increments.

SUMMARY

A first aspect of the disclosure is a method of calibrating a microbolometer focal plane array (MFPA) having detector elements and that resides in a thermal camera that has a processing unit that is operably coupled to an external computer. The method includes: a) determining reference and detector non-uniformity corrections (NUCs) in the processing unit based on reference voltages from the MPFA, and applying the reference and detector NUCs to the detector elements as coarse corrections that establish a coarse calibration, and sending the reference and detector NUCs to the external computer. The method also includes: b) in a first measurement step, collecting image data DL1 and DH1 at respective first ambient and first calibration temperatures, and collecting image data DL2 and DH2 at respective second ambient and second calibration temperatures, and sending image data DL1, DH1, DL2 and DH2 to the external computer. The method additionally includes: c) calculating in the external computer fine corrections based on the collected image data DL1, DH1, DL2 and DH2 and the reference and detector NUCs. The method also includes: d) sending the fine corrections from the external computer to the processor unit and applying the fine corrections to the detector elements to establish a fine calibration.

Another aspect of the disclosure includes the method described above, wherein calculating the fine corrections in the external computer further comprises calculating from collected image data DL1, DH1, DL2 and DH2 gain values based on a gain slope and a gain intercept, and calculating offset values based on an offset slope and an offset intercept.

Another aspect of the disclosure includes the method described above, wherein the first and second ambient temperatures differ by a temperature increment δT, and wherein the first and second calibration temperatures differ by the temperature increment δT.

Another aspect of the disclosure includes the method described above, wherein δT=4° C.

Another aspect of the disclosure includes the method described above, further comprising repeating acts a) through d) for additional measurement steps that sequentially increment the first and second ambient temperatures and the first and second calibration temperatures by a temperature increment δT.

Another aspect of the disclosure includes the method described above, wherein the reference and detector NUCs are defined by a six-bit numbers for each detector element, wherein the first bit is a sign bit and the remaining five bits define a 0 to 32 bias voltage increment.

Another aspect of the disclosure includes the method described above, wherein the first and second calibration temperatures are maintained about 20C.° higher than the first and second ambient temperatures, respectively.

Another aspect of the disclosure includes a method of calibrating a MFPA having detector elements and that resides in a thermal camera that has a processing unit that is operably coupled to an external computer. The method includes performing first calculations in the processor unit to generate a set of coarse correction bias voltages, and applying the coarse correction bias voltages to the detector elements. The method also includes performing calculations in the external computer based on image data collected by the thermal camera with the coarse correction bias voltages applied to the detector elements to generate a set of fine correction bias voltages. The method also includes downloading the fine correction bias voltages and applying the fine correction voltages to the detector elements to establish a fine calibration of the MFPA.

Another aspect of the disclosure includes the method described above, wherein performing the first calculations includes determining reference and detector NUCs.

Another aspect of the disclosure includes the method described above, wherein performing the second calculations includes calculating gain and offset values based on image data collected at four different temperatures.

It is to be understood that both the foregoing general description and the following detailed description present embodiments of the disclosure and are intended to provide an overview or framework for understanding the nature and character of the disclosure as it is claimed. The accompanying drawings are included to provide a further understanding of the disclosure and are incorporated into and constitute a part of this specification. The drawings illustrate various embodiments of the disclosure and together with the description serve to explain the principles and operations of the disclosure.

BRIEF DESCRIPTION OF THE DRAWINGS

FIG. 3 is a schematic diagram of an example MPFA and includes a close-up inset that shows the detector elements that are electrically addressable via electrical lines;

FIG. 4 is a close-up view of an example processor unit that includes an FPGA, a memory and a timing circuit;

DETAILED DESCRIPTION

Figure 1:
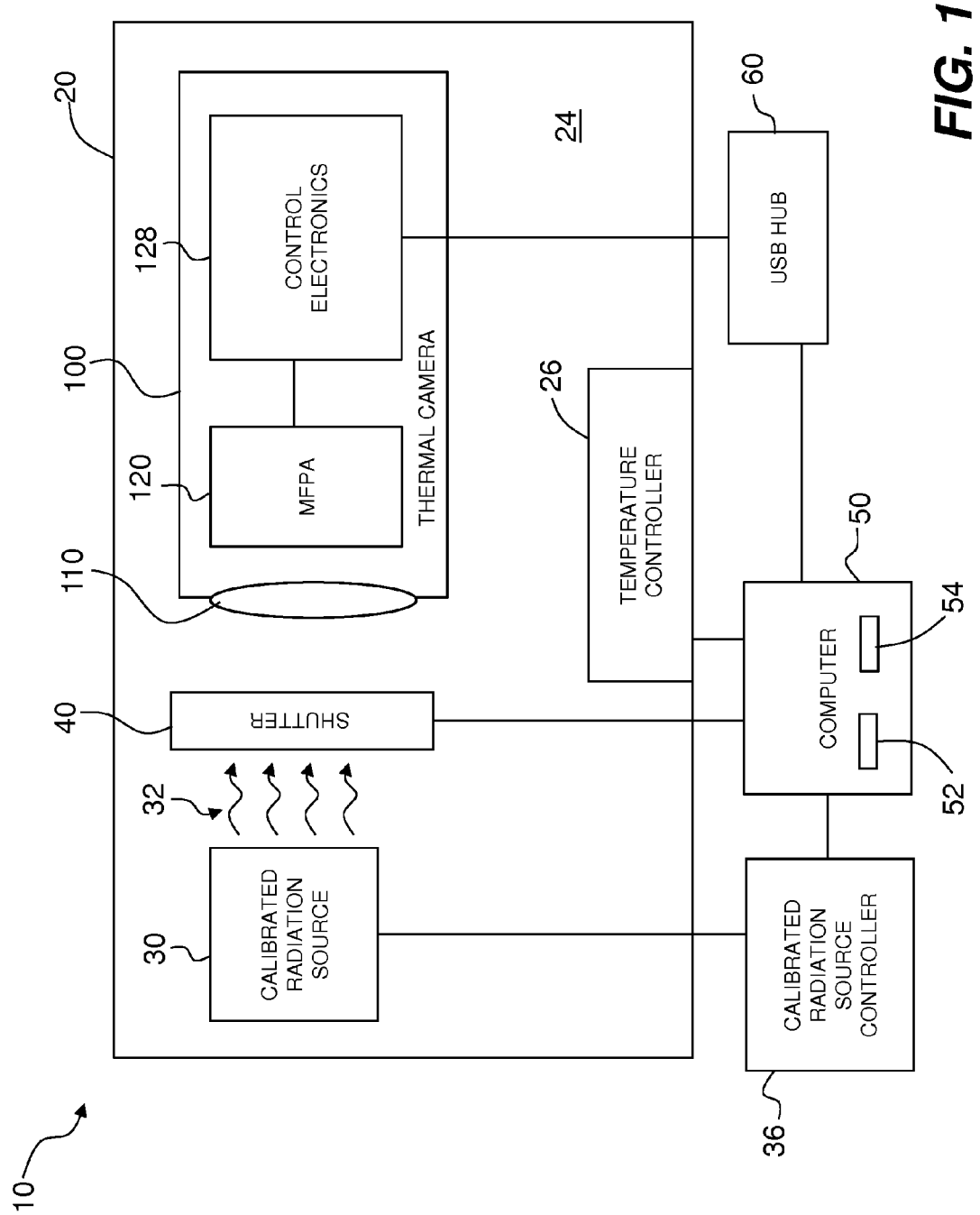
FIG. 1 is a schematic diagram of an example calibration system for calibrating the MFPA of a thermal camera.

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure. In some of the Figures, Cartesian coordinates are provided for the sake of reference and are not intended as providing limitations on specific directions and orientations of the systems and methods described herein.

The claims as set forth below are incorporated into and constitute part of this detailed description.

The term computer as used herein includes a device, for example, a floppy disk drive, CD-ROM drive, DVD drive, magnetic optical disk (MOD) device (not shown), or any other digital device including a network connecting device such as an Ethernet device (not shown) for reading instructions and/or data from a computer-readable medium, such as a floppy disk, a CD-ROM, a DVD, a MOD or another digital source such as a network or the Internet, as well as yet to be developed digital means. In another embodiment, the computer executes instructions stored in firmware (not shown). The computer is programmable to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Software may implement or aid in performing the disclosed calibration methods in the external computer or the processor unit described below. Software functionalities may involve programming, including executable code, and such functionalities may be used to implement the methods disclosed herein. Such software code is executable by the general-purpose computer or by the processor unit described below. In operation, the code and possibly the associated data records are stored within a general-purpose computer platform, within the processor unit, or in local memory. At other times, however, the software may be stored at other locations and/or transported for loading into the appropriate general-purpose computer systems. Hence, the embodiments discussed above involve one or more software products in the form of one or more modules of code carried by at least one machine-readable medium. Execution of such code by a processor of the computer system or by the processor unit enables the platform to implement the catalog and/or software downloading functions, in essentially the manner performed in the embodiments discussed and illustrated herein.

The external computer and processor unit each employ a computer-readable medium or machine readable medium which refers to any medium that participates in providing instructions to a processor for execution. Any memory discussed below constitutes a computer-readable medium. Such a medium may take many forms, including but not limited to, non-volatile media, volatile media, and transmission media. Non-volatile media include, for example, optical or magnetic disks, such as any of the storage devices in any computer(s) operating as one of the server platform, discussed above. Volatile media include dynamic memory, such as main memory of such a computer platform. Physical transmission media include coaxial cables; copper wire and fiber optics, including the wires that comprise a bus within a computer system. Common forms of computer-readable media therefore include, for example: a floppy disk, a flexible disk, hard disk, magnetic tape, any other magnetic medium, a CD-ROM, DVD, any other optical medium, less commonly used media such as punch cards, paper tape, any other physical medium with patterns of holes, a RAM, a PROM, and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Calibration System

FIG. 1 is a schematic diagram of a calibration system 10 for calibrating a thermal camera 100. Calibration includes an environmental chamber 20 having a temperature-controlled interior 24. Interior 24 is sized to accommodate an adjustable calibrated radiation source 30, which in an example is a black-body radiation source whose temperature can be adjusted to provide select black-body radiation 32. The calibrated radiation source 30 is assumed to be a black-body source in the example of calibration system 10 of FIG. 1. Calibrated radiation source 30 is controlled by a calibrated radiation source controller 36.

Environmental chamber interior 24 is also sized to accommodate at least one thermal camera 100 that has an imaging lens 110, an MFPA 120 and control electronics 128, all operably arranged as known in the art. Thermal camera 100 is arranged relative to calibrated radiation source 32 to receive and image radiation 32. In an example, interior 24 can accommodate multiple thermal cameras 100 for simultaneous calibration.

An adjustable shutter 40 (e.g., an iris) is disposed between calibration light source 30 and thermal camera 100. In an open state, shutter 32 allows radiation 32 to pass to thermal camera 100 and in a closed state it blocks the radiation from reaching the thermal camera.

The temperature of environmental chamber interior 24 is controlled by a temperature controller 26. The temperature within interior 24 is referred to herein as the ambient temperature, and in an example is maintained 20° C. below the calibrated radiation source temperature.

Calibration system 10 also includes an external computer 50 that is operably connected to temperature controller 26, calibration light source controller 36, shutter 40 and thermal camera 100 via a USB hub 60 to which additional thermal cameras being calibrated within environmental chamber interior 24 can be operably connected.

External computer 50 is configured to control the operation of the devices in calibration system 10 to carry out the methods of calibrating thermal camera 100 as described in greater detail below. As noted above, computer 50 is represented as a general purpose computer, and can be any type of computer, such as a personal computer (PC), work station, etc., that has processing and memory capability and that can operate under the direction of software. External computer 50 includes a processor 52 and a memory 54.

Figure 2:
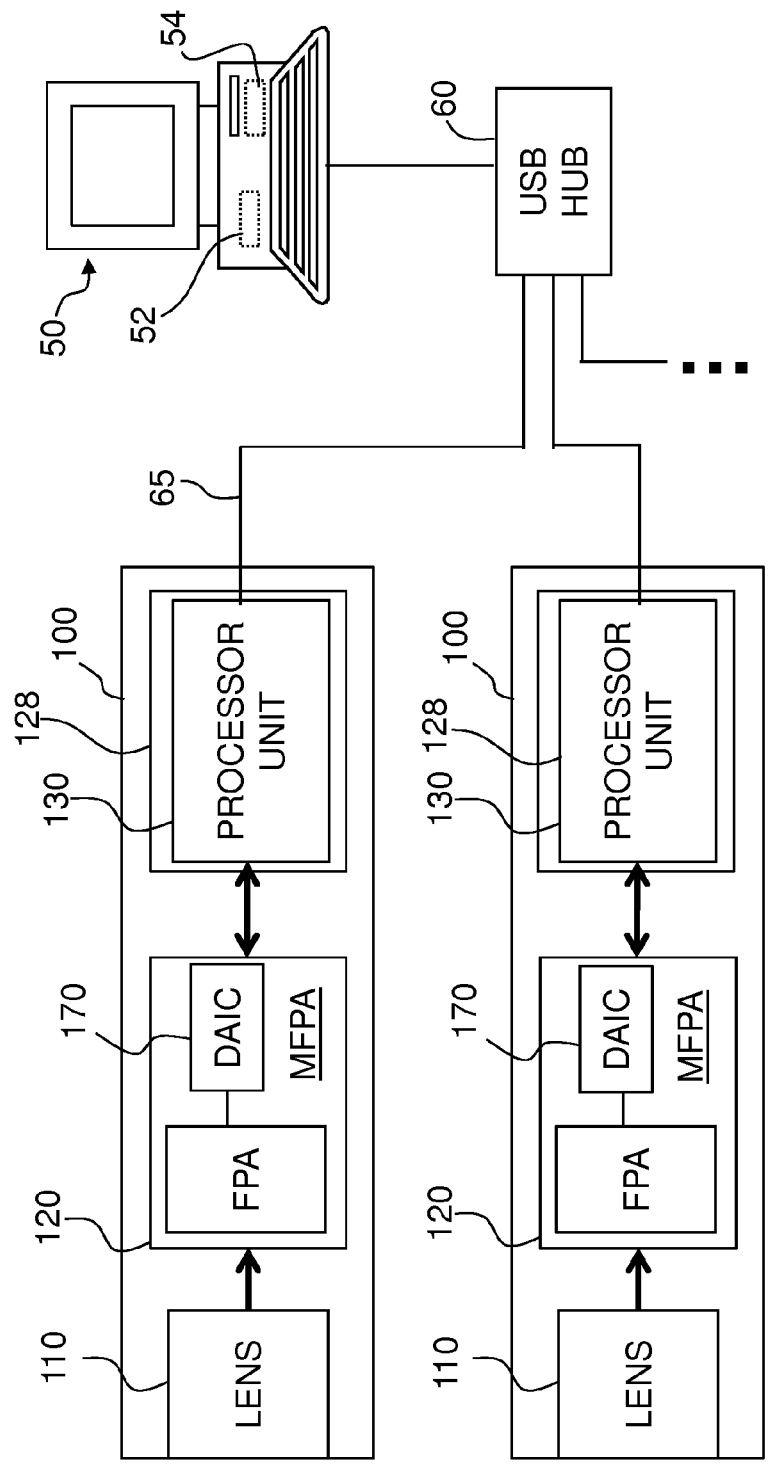
FIG. 2 is a schematic diagram of two thermal cameras operably connected to an external computer via electrical lines and a USB hub.

FIG. 2 is a schematic diagram showing an example arrangement of two thermal cameras 100 operably connected to external computer 50 via USB hub 60 via USB cables 65. The environmental chamber 20 and other components such as the calibration light source 30 are omitted from FIG. 2 for ease of illustration.

Thermal camera 100 includes the aforementioned imaging lens 110, which in an example is compound lens configured to transmit infrared wavelengths of light used in thermal imaging. Imaging lens 110 is configured to collect infrared radiation 32 from calibrated radiation source 30 (or more generally from a scene or other source of radiation) and form an image onto MFPA 120. With reference also to FIG. 3, MFPA 120 includes a two-dimensional FPA 150 comprised of an M×N array of thermally-isolated microbolometer detector elements ("detector elements") 152 operably supported on a substrate 160, such as a semiconductor substrate. MFPA 120 includes on substrate 160 integrated circuit architecture, such as a detector array interface circuit (DAIC) 170 (shown in phantom in FIG. 3) electrically connected to detector elements 152 via electrical lines 164 and configured to provide a bias voltages and detector output multiplexing functions. It is noted here that in an example some detector elements 152 are reference detector elements that are configured so that they are not exposed to incident radiation. Reference detector elements 152 allow for reference (blind) measurements to be taken, as discussed below. Unless otherwise noted, detector elements 152 are assumed to be "active" detector elements that are exposed to and respond to radiation 32.

The control electronics 128 of thermal camera 100 includes a processor unit 130 electrically connected to DAIC 170 and whose function is described in greater detail below. An example processor unit 130 is schematically illustrated in FIG. 4 and includes a field-programmable gate array (FGPA) processor 132, a memory unit 134 (e.g., ROM, RAM, SRAM, etc.), and a microprocessor 136, as well as other electronic components known in the art that are not shown. FGPA processor 132 is configured to carry out control operations and perform data processing calculations for the on-board portion of the calibration methods as described below.

With reference again to FIG. 3, substrate 160 may also support one or more of the aforementioned electrical lines 164, which are configured so that electrical signals (e.g., bias voltages) may be communicated to each detector element and output signals (e.g., output voltages) may be communicated to DAIC 170 from the detector elements. Only a single electrical line 164 is shown for ease of illustration, and there may be multiple such electrical lines connected to each detector element. By way of example, each detector element 152 may be manufactured as a microbridge, such as described in the aforementioned U.S. Pat. No. 5,286,976. Such detector elements 152 are manufactured directly onto the substrate by known methods.

Detector signals from each detector element 152 in FPA 150 are preferably time multiplexed to reduce the number of pins required. The electrical inputs to focal plane array 150 in turn are the biasing signals (e.g., bias voltages) needed to bias the detector elements 152 and drive the DAIC 170 and signals to control the readout of signals from the array. Detector elements 152 also receive coarse correction signals (bias voltages) via electrical lines 164, which allow individualized correction of non-uniformities in each detector element of the array, as discussed in more detail below.

In an example, DAIC 170 performs any analog filtering or other analog conditioning which may be desired on the analog detection signals. DAIC 170 can also perform an analog to digital conversion to form a desired number of bits of image data for each detector element 152 of the array. Since the detection signals are preferably in the form of time-multiplexed signals for each detector element 152 (for example provided on a row-by-row basis), the DAIC 170 will analog-to-digital convert such signals on a corresponding time-multiplexed basis and read the image data into a buffer memory (not shown). For example, a commercially available RAM of suitable size (i.e., having storage capacity equal to the number of pixels in the array times number of bits per pixel) may be employed.

After storage in a buffer memory (not shown), additional digital conditioning may be performed on the raw image data. The digital processed image data is then provided to processor 130. For example, the image data may be provided in Q bit parallel fashion, where Q is the number of sample bits for each detector element 152. Alternatively, the image data may be provided in a serial fashion to processor unit 130. It is noted that some of the above operations can also be performed by processor unit 130 rather than in DAIC 170.

As noted above, DAIC 170 also provides the appropriate analog biasing voltages (and/or currents) to detector elements 152 in focal plane array 150. Accordingly, in an example, DAIC 170 includes the appropriate bias-signal generating circuitry. The analog-to-digital conversion circuitry, buffer memory, and biasing circuitry employed in DAIC 170 may be conventional in nature and accordingly are not described in more detail herein.

Since DAIC 170 typically includes a number of discrete components, it is preferably formed as a printed circuit board. It will be appreciated, however, that alternate embodiments may also be employed such as discrete components mounted in another manner or a suitable VLSI circuit incorporating both analog and digital capabilities, for example, in a so-called BiCMOS architecture.

Processor unit 130 is configured to provide intelligent control of FPA 150 and also to perform signal processing, as well as perform the aforementioned on-board calculations relating to the coarse calibration of detector elements 152, as described below, and to apply the fine calibration data to the detector elements.

Calibration Methods

As discussed above, the conventional methods of performing a calibration of detector elements 152 is time consuming. Accordingly, aspects of the disclosure are directed to non-uniformity correction (NUC) methods for calibrating detector elements 152 of MFPA that take advantage of the standalone processing capabilities of the thermal camera's control board as represented by processor unit 130.

Calibration system 10 is used to obtain offset and gain information associated with each of detector element 152 by subjecting the detector elements to radiation 32 having known wavelengths and known intensity characteristics. Ideally, detector elements 152 all view the same uniform radiation 32, which permits gain and offset information associated with each of the detector elements to be derived by a calibration process. The calibration methods disclosed herein eliminate the time consuming upload/download/flash-write cycles.

Instead, NUC calculations for coarse calibration are performed on board in thermal camera 100 in processor unit 130 and the NUC data is stored to local memory (i.e., SRAM) 134, while a fine calibration calculation is performed externally in external computer 50. This enables the NUC process to be performed significantly faster while also permitting multiple thermal cameras to be calibrated in parallel in calibration system 10. This is made possible by eliminating time-consuming computer communications and calculations, including eliminating the relatively slow flash memory data writing, which bottleneck the calibration process.

The calibration methods disclose herein allow a user to place multiple thermal cameras 100 in interior 24 of environmental chamber 20. Each thermal camera 100 has stand-alone NUC processing capability via their respective processor units 100, which are configured to perform the iterative steps required for a thermal camera non-uniformity correction calibration.

The reduction in calibration processing time is accomplished in part by having the processor unit 100 of each individual camera collect and process its own image data. The image data is quickly collected and stored in faster SRAM of memory 134 of processor unit 130, and then is immediately processed through on-board FPGA "state-machines" 132 configured in each of the thermal camera's processing units 130, which are programmed to determine the next iterative set of NUC values to apply to the imager array. These new NUC values are then immediately stored in SRAM memory 134 for processor unit 130 to receive and process in real-time so that the next iterative data point is collected. In this manner, no data communication is necessary with external computer 50 during the iterative NUC determination process.

The total NUC determination process is beneficially reduced down to about several minutes, rather than multiple hours by using the parallel processing capability of the respective processor units 130 in the thermal cameras 100 and eliminating the multiple and time-consuming data communications with the external processing external computer 50. Once the final NUC values are determined, the NUC data are sent to external computer 50 only once for the software therein to calculate the fine corrections and send back the fine correction calibration data to the thermal camera, which stores this fine correction calibration data in (flash) memory 134. A copy of the data may also be stored in memory 54 of computer 50.

Image Data Collection and Calibration

Figure 5:
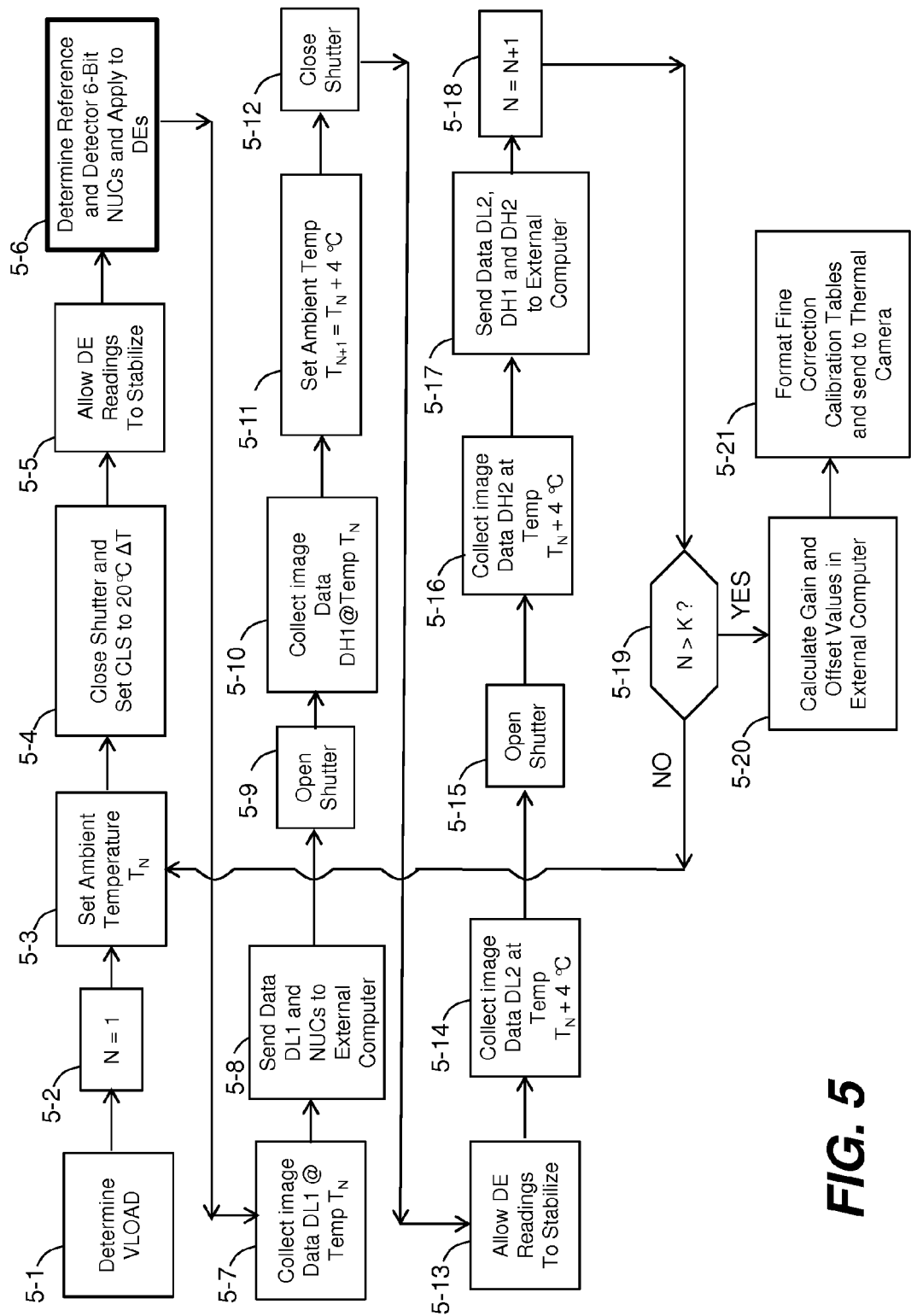
FIG. 5 is a flow diagram of an example calibration process according to the disclosure, wherein a coarse calibration is performed onboard the thermal camera in the processing unit while a fine calibration is performed in the external computer.

FIG. 5 is a flow diagram that outlines the calibration process. In step 5-1, the optimum value of VLOAD is determined. This step is performed according to conventional practice and is usually conducted per the recommendations of the MFPA manufacturer. Generally, the optimum value of VLOAD corresponds to a bias voltage applied to all of detector elements 152 that maximizes the high and low temperature response of the detector elements (which are abbreviated as DE in the flow diagram).

Then in step 5-2, the number N of the calibration measurement is set to N=1 for the first measurement. In step 5-3, the ambient temperature $T_N$ is set in environmental chamber interior 24 via the operation of temperature controller 26. In step 5-4, shutter 40 is closed via the operation external computer 50, and calibrated radiation source (abbreviated as CLS in the flow diagram) is set to a black-body temperature that is 20° C. greater than the ambient temperature $T_N$. A first example black-body temperature is −20° C. In step 5-5, the readings from detector elements 152 are allowed to stabilize.

In step 5-6, the reference and detector NUC 6-bit values are determined and the final NUC values are applied to the detector elements 152 and are also saved to a data file. The details of step 5-6 are discussed in greater detail below in the flow diagrams of FIGS. 6 and 7. The application of the reference and detector NUCs are applied to detector elements 152 as a coarse correction bias voltage.

In step 5-7, image data from detector elements 152 (now with the reference and detector NUCs applied as a coarse calibration) are collected at the ambient temperature with shutter 40 closed. These image data DL1 ("first low temperature image data") are stored electronically in memory 134 of processor unit 130. In step 5-8, image data DL1 along with the reference and detector NUC data are sent to external computer 50 for processing to determine the fine corrections for performing fine calibration.

In step 5-9, shutter 40 is opened, and in step 5-10, thermal camera 100 collects image data based on calibration radiation 32 from calibrated radiation source 30, and these image data DH1 ("first high temperature data") are stored electronically in memory 134.

Next in step 5-11, the ambient temperature in environmental chamber interior 24 is increased by a temperature increment δT, such as δT=4° C., and in 5-12 shutter 40 is closed. Then in step 5-13, the readings from detector elements 152 are allowed to stabilize. In step 5-14, image data DL2 (second low temperature data") from detector elements 152 are collected at the ambient temperature with shutter 40 closed and are stored electronically.

In step 5-15, shutter 40 is opened, and in step 5-16, thermal camera 100 collects image data DH2 ("second high temperature data") based on calibration radiation 32 from calibrated radiation source 30 with the temperature of the calibrated radiation source increased by 4° C. from its previous setting to maintain the 20° C. differential between ambient and calibration source temperature. Thus, four sets of data: DL1, DL2, DH1 and DH2 are collected and stored in memory 134 on board thermal camera 100 in processor unit 130. In Step 5-17, after DH2 is collected, image data DL2, DH1 and DH2 are sent to external computer 50.

Step 5-18 increments the measurement number N by 1 and step 5-19 asks whether K measurements have been made. An example number N of measurements is 18. If N<K, then the process from steps 5-3 through 5-17 are repeated.

Note that after say N=18 steps, there will be 18 tables of 6-bit NUC values, which are each tied to the low ambient temperature data DL1 for the given measurement iteration. Note also that the 6-bit values are applied to each detector element 152 in step 5-6 for each measurement iteration and represent a coarse calibration for the corresponding ambient temperatures. An example temperature range for taking calibration measurements is from −20° C. to 52° C. in δT=4° C. increments.

When N>K, the temperature measurements are completed. At this point, per step 5-8, the tables that contain the 6-bit NUC values for each measurement iteration have been uploaded to external computer 50 along with image data DL1, and per step 5-17, image data DL2, DH1 and DH2 have been sent. Thus, in step 5-20, external computer calculates the gain and offset values as described below based on the image data. Then in step 5-21, external computer 50 generates formatted calibration tables that include the fine corrections where the gain and offset values are added to the coarse corrections and provided to processor unit 130, which applies the fine corrections to detector elements 152. This results in thermal camera 100 (and specifically MFPA 120 therein) having a fine calibration.

Figure 6:
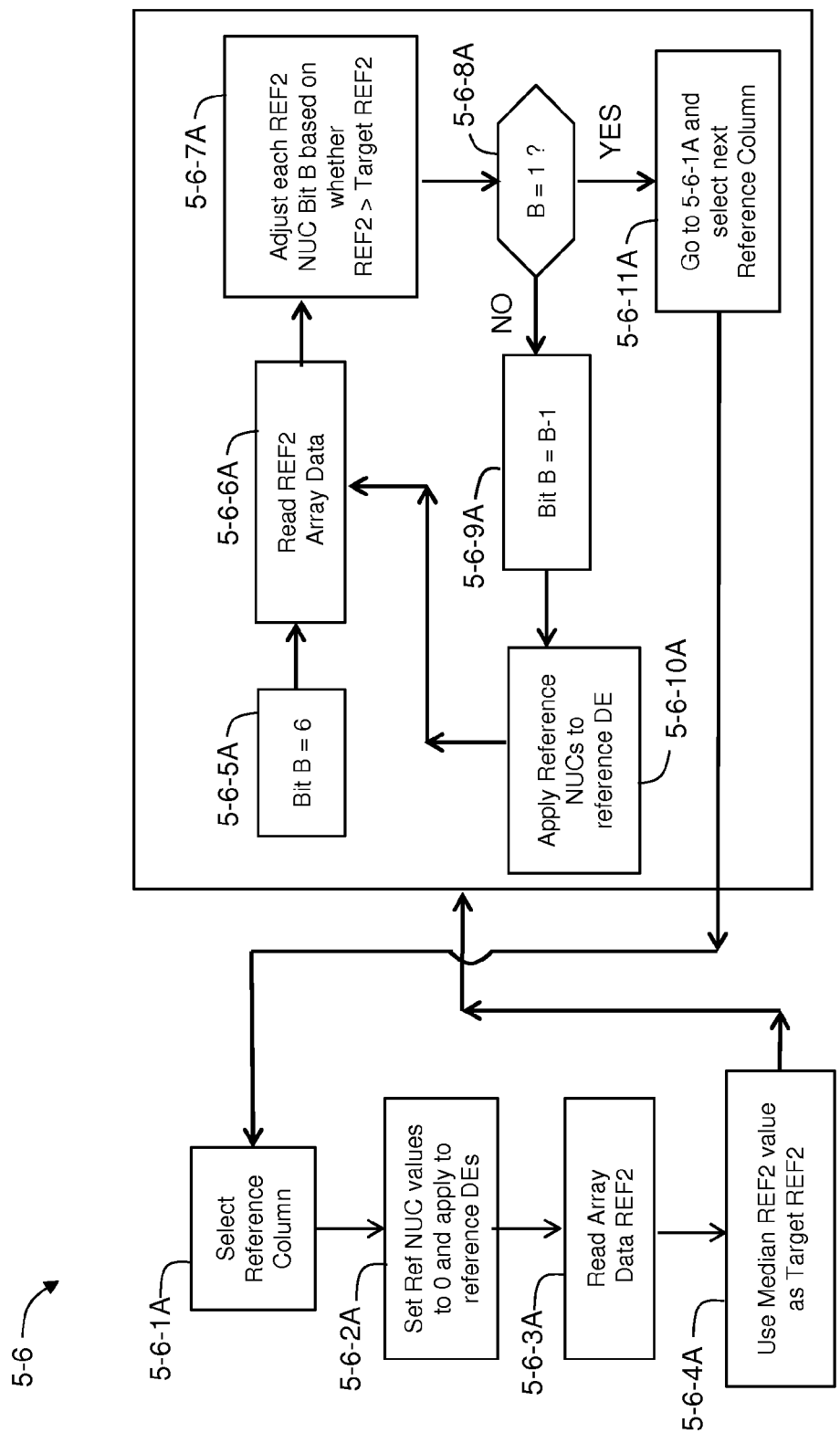
FIG. 6 and FIG. 7 are flow diagrams of example processes for determining the reference and detector non-uniformity correction (NUC) values, respectively, as part of the calibration process of FIG. 5.

FIG. 6 is a flow diagram that sets forth the steps carried out by processor unit 130 for determining reference NUCs per step 5-6 of FIG. 5. In step 5-6-1A, a column of the aforementioned reference detector elements 152 are selected. In an example, there are eight such reference columns. In step 5-6-2A, all of the NUC values are set to zero and applied to the reference detector elements. Then in step 5-6-3A, a REF2 value is read, where the REF2 value is a combination of (e.g., the sum of) the voltage from a heat-sunk detector element and a reference detector element and thus provides the output voltage for the enabled reference detector elements.

In step 5-6-4A, a median signal value (or an average signal value, as the case may be) ("median REF2 value") is obtained that is used as a target REF2 value (the REF2 value at the optimum VLOAD bias voltage) to normalize all of the reference detector elements. The details of step 5-6-4A are shown in the larger box in steps 5-6-5A through 5-6-11A, which acts on all of the detector elements in the given reference column.

In the particular example, each detector element 152 is associated with a six NUC bits B, with the first bit being a sign bit that tells whether corrections are added to or subtracted from the particular reference detector element. The remaining five bits define a hexadecimal number that ranges from 0 to 32, which represents the granularity of the correction that can be applied. As this granularity is relatively coarse, it is associated with making a coarse correction, which is applied to the reference detector elements as a bias voltage.

Thus, the six NUC bits B are adjusted for each reference detector element in the reference columns so that each of these detector elements has an output voltage that is as close as possible to the median value of the output voltage. In particular, in step 5-6-7A, each NUC bit B in the six-bit number is adjusted given whether value ("REF2") is greater than the median value or "target REF2". The reference NUCs are then applied to the particular reference detector elements in the column, per step 5-6-10A, as first coarse correction bias voltages. This process is repeated for each column of reference detector elements.

Figure 7:
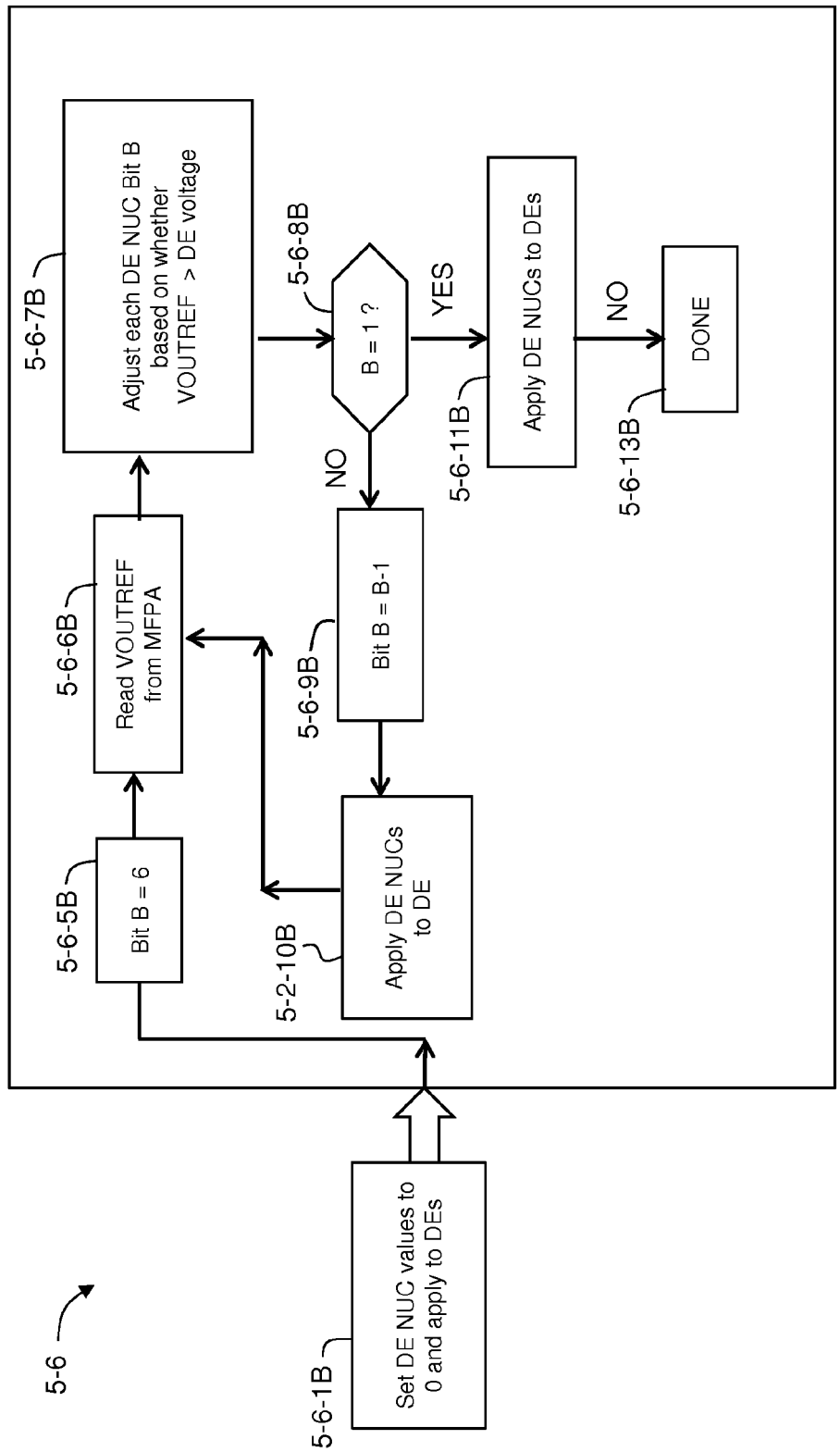

FIG. 7 is a flow diagram similar to that shown in FIG. 6 and illustrates a similar example process for determining the NUCs for the non-reference detector elements 152 in accordance with step 5-6 of the flow diagram of FIG. 5. Thus, in step 5-6-1B, the NUC values for the non-reference (i.e., active) detector elements (hereinafter, just "detector elements") 152 are set to 0 and applied to the detector elements. Then step 5-6-6B involved reading voltage VOUTREF, which is the output reference level for all of the detector elements. VOUTREF thus serves as a target reference voltage for establishing the detector element NUCs.

In step 5-6-7B, each detector element has its NUC bits adjusted depending on whether VOUTREF>DE output voltage for the particular detector element, in similar fashion to the process described in FIG. 6.

In steps 5-6-7B through 5-6-11B, the detector NUCs are then applied to each detector element 152 on a bit-by-bit basis until there are no more bits to process. It is noted here that if an abnormal column is detected, its heat-sunk detector element is replaced and the detector NUC process is started from the beginning. Once all of the bits are done, then the process terminates in step 5-6-13B, and the detector NUCs are established and applied to detector elements 152 as a coarse correction bias voltage for the given measurement iteration. As discussed above, the reference and detector NUC 6-bit values are stored in 18 tables (files) in memory 134 of processor unit 130.

It is emphasized here that the processes for determining the reference NUCs and the detector NUCs for step 5-6 of FIG. 5 as set forth in more detail in FIGS. 6 and 7 respectively are performed on-board thermal camera 100 in processor unit 130. The six-bit reference NUCs and detector NUCs represent a coarse correction to detector elements 152 in FPA 150 for each 4° C. temperature increment. The six-bit coarse corrections (which have a range from 0 to 32 that is translated into bias voltages of like increments) are applied to each detector element 152 for the 4° C. span. This information is then sent to external computer 50 (step 5-8 of FIG. 5), where it is stored. External computer 50 then performs a fine correction over the low and high temperature ranges and then sends back a calibration table with the fine correction data. This fine correction data is then applied to each detector element to achieve fine correction (and thus a fine calibration) of the MFPA 120.

Gain and Offset Values

The calibration process illustrated in FIG. 5 includes in step 5-20 the calculating of the gain and offset values needed for the fine correction for each N ambient temperature measurement calibration ("CAL") table. This is carried out in external computer 50 after all N ambient temperature measurements have been processed.

The following variables are used in the calculation of the gain and offset values which involve calculating the gain slope $S_G(x,y)$, the gain intercept $INT_G(x,y)$, the offset slope $S_O(x,y)$, and the offset intercept $INT_O(x,y)$, with (x,y) denoting the particular detector element 152 in FPA 150:

DL1=ambient temperature image data with shutter closed
DH1=ambient temperature image data with shutter open
DL2=ambient temperature image data with a +4° C. increment with shutter closed
DH2=ambient temperature image data with a +4° C. increment with shutter open
T1=ambient temperature at bottom of temperature range
T2=ambient temperature at top of temperature range (approximately T1+4° C.)
$\mu_{11}$=mean of the elements (DH1−DL1) that are within +/−2 standard deviations
$\mu_{22}$=mean of the elements (DH2−DL2) that are within +/−2 standard deviations
$\mu_1$=mean of the elements DL1 that are within +/−2 standard deviations
(x,y)=image array coordinate $$DH1-DL1=\Delta_{11}$$

$$DH2-DL2=\Delta_{22}$$

$$T2-T1=\Delta T$$

The equations for the gain slope and intercept $S_G(x,y)$ and $INT_G(x,y)$ are given by:

$$S_G(x,y)=[\{\mu_{22}\cdot[\Delta_{22}]^{-1}\cdot(2048)-\mu_{11}\cdot[\Delta_{11}]^{-1}\cdot(2048)\}/\Delta T]\cdot(128)+256$$

$$INT_G(x,y)=\{\mu_{11}\cdot[\Delta_{11}]^{-1}\}\cdot(2048)$$

The gain slope $S_G(x,y)$ has a range of values from 0 to 1023 while the gain intercept $INT_G(x,y)$ has a range of values from 0 to 4095. These ranges provide a much finer correction granularity than the range from 0 to 32 of the 6-bit NUCs associated with the coarse correction.

The offset slope and intercept $S_o(x,y)$ and $INT_o(x,y)$ are given by:

$$S_O(x,y)=([\{[\{\mu_1-[\mu_{22}/\Delta_{22}]\cdot DL2\}+2048]-[\{\mu_1-[\mu_{11}/\Delta_{11}]\cdot DL1\}+2048]\}\cdot(128)]\cdot(\Delta T)^{-1})+256$$

$$INT_O(x,y)=(\mu_1-\{\mu_{11}\cdot[\Delta_{11}]^{-1}\}\cdot DL1)+2048$$

The offset slope $S_O(x,y)$ has a range of data values from 0 to 1023 while the offset intercept $INT_O(x,y)$ has a range of data values from 0 to 4095. These ranges provide a much finer correction granularity than the range from 0 to 32 of the 6-bit NUCs associated with the coarse correction. An example FPA array has 330×240 detector elements.

An example program for calculating the gain and offset values for the fine correction (i.e., the NUC table post-correction coefficient) that can be run by processing unit 130 (e.g., FPGA 132 therein) is as follows:

$$gain\_t=((gain\_slope-256)/128)*(T-T0)+gain\_intercept$$

$$offset\_t=((offset\_slope-256)/128)*(T-T0)+offset\_intercept$$

$$pixel\_out=((rawpix*gain\_t)/2048)+offset\_t-2048$$

wherein:
T=current temperature of FPA 150
T0=base temperature T1 for a current NUC calibration (CAL) table
offset_slope=$S_O(x,y)$
offset_intercept=$INT_O(x,y)$
gain_slope=$S_G(x,y)$
gain_intercept=$INT_G(x,y)$
rawpix=detector element output voltage with 6-bit coarse NUC applied
pixel_out=corrected pixel value with coarse and fine NUC corrections If the 6-bit NUC data were to be calculated on external computer 50 as might be done in the prior art approach, it takes on the order of 240 seconds to upload the data and perform the NUC reference and detector calculations. Conversely, this calculation takes about 1.5 seconds when performed in the thermal camera's on-board processing unit 130, representing a time savings factor of 160×.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by any claims in any subsequent application claiming priority to this application.

For example, notwithstanding the fact that the elements of such a claim may be set forth in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a subsequent claim must be understood as being generic to all possible meanings supported by the specification and by the word itself.

The definitions of the words or elements of any claims in any subsequent application claiming priority to this application should be, therefore, defined to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements in such claims below or that a single element may be substituted for two or more elements in such a claim.

Although elements may be described above as acting in certain combinations and even subsequently claimed as such, it is to be expressly understood that one or more elements from a claimed combination can in some cases be excised from the combination and that such claimed combination may be directed to a subcombination or variation of a subcombination.

Insubstantial changes from any subsequently claimed subject matter as viewed by a person with ordinary skill in the art, now known or later devised, are expressly contemplated as being equivalently within the scope of such claims. Therefore, obvious substitutions now or later known to one with ordinary skill in the art are defined to be within the scope of the defined elements.

What is claimed is:

1. A method of calibrating a microbolometer focal plane array (MFPA) having detector elements and that reside in a thermal camera that has a processing unit that is operably coupled to an external computer and a shutter, comprising:
   determining, in the processing unit, detector non-uniformity corrections (NUCs) for corresponding ones of the detector elements based on reference voltages from the MFPA;
   applying the detector NUCs to the detector elements as coarse corrections that establish a coarse calibration;
   sending the detector NUCs to the external computer;
   in a first measurement step:
      collecting image data DL1 at a first ambient temperature and image data DH1 at a first calibration source temperature;
      collecting image data DL2 at a second ambient temperature and image data DH2 at a second calibration source temperature; and
      sending image data DL1, DH1, DL2 and DH2 to the external computer;
   calculating, in the external computer, fine corrections based on the collected image data DL1, DH1, DL2 and DH2 and the detector NUCs; and
   sending the fine corrections from the external computer to the processor unit and applying the fine corrections to the detector elements to establish a fine calibration.

2. The method of claim 1, wherein calculating the fine corrections in the external computer further comprises calculating from collected image data DL1, DH1, DL2 and DH2 gain values based on a gain slope and a gain intercept, and calculating offset values based on an offset slope and an offset intercept.

3. The method of claim 1, wherein the first and second ambient temperatures differ by a temperature increment δT, and wherein the first and second calibration source temperatures differ by the temperature increment δT.

4. The method of claim 3, wherein δT =4° C.

5. The method of claim 1, wherein the determining the detector NUCs, applying the detector NUCs, sending the detector NUCs, and the first measurement step are repeated for additional measurement steps that sequentially increment the first and second ambient temperatures and the first and second calibration source temperatures by a temperature increment δT.

6. The method of claim 5, wherein the additional measurement steps are completed before the calculating fine corrections and sending the fine corrections are performed.

7. The method of claim 1, wherein the detector NUCs are defined by a six-bit numbers for each detector element, wherein the first bit is a sign bit and the remaining five bits define a 0 to 32 bias voltage increment.

8. The method of claim 1, wherein the first and second calibration source temperatures are maintained about 20 C.° higher than the first and second ambient temperatures, respectively.

9. The method of claim 1, wherein the image data DL1 is obtained at the first ambient temperature with the shutter closed, image data DH1 is obtained at the first ambient temperature with the shutter open so that the MFPA is exposed to the first calibration source temperature, image data DL2 is obtained at the second ambient temperature with the shutter closed and image data DH2 is obtained at the second ambient temperature with the shutter open so that the MFPA is exposed to the second calibration source temperature.

10. A method of calibrating a microbolometer focal plane array (MFPA) having detector elements and that reside in a thermal camera that has a processing unit that is operably coupled to an external computer and a shutter, comprising:
   performing first calculations in the processing unit to generate a set of coarse correction bias voltages;
   applying the coarse correction bias voltages to the detector elements;
   collecting image data with the coarse correction bias voltages applied to the detector elements;
   performing second calculations in the external computer based on the image data collected by the thermal camera to generate a set of fine gain and fine offset correction values;
   downloading the fine correction values; and
   applying the fine correction values to the detector elements to establish a fine calibration of the MFPA;
   wherein performing first calculations is repeated at a plurality of ambient temperatures to calculate a plurality of coarse correction tables corresponding to various ones of the ambient temperatures, and wherein performing second calculations includes calculating fine correction values to create a plurality of fine correction tables corresponding to the various ones of the ambient temperatures.

11. The method according to claim 10 wherein performing the first calculations includes determining detector non-uniformity corrections (NUCs) for corresponding ones of the detector elements.

12. The method according to claim 10, wherein performing the second calculations includes calculating gain and offset values based on image data collected at four different temperatures.

13. The method of claim 10, wherein:
   performing first calculations includes calculating detector non-uniformity corrections (NUCs) and;
   collecting image data includes collecting image data DL1 at a first ambient temperature and image data DH1 at a first calibration source temperature, and collecting image data DL2 at a second ambient temperature and image data DH2 at a second calibration source temperature, wherein the NUCs and image data DL1 are sent to the external computer before image data DH1, DL2, and DH2 are obtained.

14. A method of calibrating a microbolometer focal plane array (MFPA) having detector elements and that reside in a thermal camera that has a processing unit that is operably coupled to an external computer and a shutter, comprising:
   performing first calculations in the processing unit to generate a set of coarse correction bias voltages;
   applying the coarse correction bias voltages to the detector elements;

collecting image data with the coarse correction bias voltages applied to the detector elements;

performing second calculations in the external computer based on the image data collected by the thermal camera to generate a set of fine gain and fine offset correction values;

downloading the fine correction values; and applying the fine correction values to the detector elements' output signals to establish a fine calibration of the MFPA;

wherein:

performing first calculations includes calculating detector non-uniformity corrections (NUCs); and collecting image data includes:

collecting image data DL1 at a first ambient temperature and image data DH1 at a first calibration source temperature; and collecting image data DL2 at a second ambient temperature and image data DH2 at a second calibration source temperature, wherein the NUCs and image data DL1 are sent to the external computer before image data DH1, DL2, and DH2 are obtained.

15. The method according to claim 14, wherein performing the second calculations includes calculating gain and offset values based on image data DL1, DL2, DH1, and DH2.

16. The method of claim 14, wherein DL1 and DL2 are obtained with the shutter closed and DH1 and DH2 are obtained with the shutter opened.

17. The method of claim 14, wherein performing first calculations is repeated at a plurality of ambient temperatures to calculate a plurality of coarse correction tables corresponding to various ones of the ambient temperatures, and wherein performing second calculations includes calculating fine correction values to create a plurality of fine correction tables corresponding to the various ones of the ambient temperatures.

* * * * *